US00RE36399E

United States Patent [19]

Honeycutt

[11] E Patent Number: Re. 36,399

[45] **Reissued Date of Patent: *Nov. 23, 1999**

[54] METHOD OF DISPOSAL OF HOT WATER SOLUBLE UTENSILS

[75] Inventor: Travis W. Honeycutt, Norcross, Ga.

[73] Assignee: Isolyser Company, Inc., Norcross, Calif.

[ * ] Notice: This patent is subject to a terminal disclaimer.

[21] Appl. No.: 08/427,555

[22] Filed: Apr. 24, 1995

Related U.S. Patent Documents

Reissue of:

[64] Patent No.: 5,181,967
Issued: Jan. 26, 1993
Appl. No.: 07/884,806
Filed: May 19, 1992

U.S. Applications:

[63] Continuation-in-part of application No. 07/739,902, Aug. 2, 1991, abandoned.

[51] Int. Cl.[6] ..... B08B 7/00

[52] U.S. Cl. ..... 134/42

[58] Field of Search ..... 134/42

[56] References Cited

U.S. PATENT DOCUMENTS

| | | | |
|---|---|---|---|
| 3,413,229 | 11/1968 | Bianco | 252/90 |
| 3,484,874 | 12/1969 | Bickenheuser, Jr. | 4/112 |
| 3,762,454 | 10/1973 | Wilkins, Jr. | 150/1 |
| 3,859,125 | 1/1975 | Miller et al. | 428/511 |
| 3,886,610 | 6/1975 | Shelden | 5/81 R |
| 4,295,850 | 10/1981 | Haberli et al. | 252/90 |
| 4,372,311 | 2/1983 | Potts | 128/287 |
| 5,051,222 | 9/1991 | Marten et al. | 264/143 |
| 5,181,966 | 1/1993 | Honeycutt et al. | 134/42 |
| 5,207,837 | 5/1993 | Honeycutt | 134/42 |

FOREIGN PATENT DOCUMENTS

| | | |
|---|---|---|
| 8902229 | 1/1990 | Brazil . |
| 0050288 | 10/1981 | European Pat. Off. . |
| 0107576 | 5/1984 | European Pat. Off. . |
| 0176316 | 4/1986 | European Pat. Off. . |
| 0272816 | 6/1988 | European Pat. Off. . |
| 1519530 | 4/1970 | Germany . |
| 3017246 | 11/1981 | Germany . |
| 47-41741 | 10/1972 | Japan . |
| 55-71532 | 5/1980 | Japan . |
| 59-100704 | 6/1984 | Japan . |
| 60-44897 | 3/1985 | Japan . |
| 61-159995 | 7/1986 | Japan . |
| 2-68396 | 3/1990 | Japan . |
| 386161 | 1/1933 | United Kingdom . |
| 743165 | 1/1956 | United Kingdom . |
| 1187690 | 4/1970 | United Kingdom . |
| 1374199 | 11/1974 | United Kingdom . |
| 1451619 | 10/1976 | United Kingdom . |
| 2102461 | 2/1983 | United Kingdom . |
| 2119709 | 11/1983 | United Kingdom . |
| 2211088 | 6/1989 | United Kingdom . |
| 2211196 | 6/1989 | United Kingdom . |
| 2248842 | 4/1992 | United Kingdom . |
| WO 91/14413 | 10/1991 | WIPO . |
| WO 91/17210 | 11/1991 | WIPO . |

OTHER PUBLICATIONS

*Encyclopedia of Polymer Science and Engineering,* vol. 17, p. 192, John Wiley & Sons, Inc., New York (1989).

*Primary Examiner*—Zeinab El-Arini
*Attorney, Agent, or Firm*—Needle & Rosenberg, P.C.

[57] ABSTRACT

A method of disposing of utensils after use. The utensils are provided as molded, formed or extruded articles which are only water soluble at temperatures above 37° C. After use, the utensils are subjected to water at a sufficient temperature to substantially dissolve them whereupon the water and dissolved articles are subjected to sewer disposal.

2 Claims, No Drawings

METHOD OF DISPOSAL OF HOT WATER SOLUBLE UTENSILS

Matter enclosed in heavy brackets [ ] appears in the original patent but forms no part of this reissue specification; matter printed in italics indicates the additions made by reissue.

CROSS-REFERENCE TO RELATED APPLICATIONS

*This application is a continuation-in-part of U.S. application Ser. No. 739,902, filed Aug. 2, 1991, abandoned.*

TECHNICAL FIELD OF THE INVENTION

The present invention involves disposable hot water soluble utensils and the method of disposing of such utensils after use. Specifically, the utensils are composed of molded, formed or extruded articles which are water soluble at temperatures above approximately normal human body temperature (37° C.) and preferably above 50° C. while most preferably between 80°—90° C.

BACKGROUND OF THE INVENTION

Hospital patient care generates considerable quantities of infectious medical waste in primary and acute care facilities. There has been a general conversion from reusable, cleanable items, to disposable items over the last three decades. These conversions were made to promote antiseptic techniques in patient care and to decrease the potential for cross-infections between patients, staff and the general public. Recent federal and state government regulations such as the Medical Waste Tracking Act of 1988 and OSHA Medical Facility rules have resulted in a substantial increase in medical waste that must be classified as "infectious."

When a patient is admitted to a hospital, the patient produces approximately 55 pounds of medical waste per day. Approximately 20% of this waste is infectious. The current stated objective of the American Hospital Association and the Centers for Disease Control is to treat medical waste as soon as it is generated. Both organizations recognize that medical waste is primarily an occupational hazard for health care workers and not an environmental problem. The best way to deal with infectious medical waste is to disinfect it at the point of generation and dispose of the treated medical waste with minimum handling and storage on premises. The need for an effective way to dispose of medical waste has been highlighted by the amendment made to 29 C.F.R. §1910.1030 which provides for the federal regulation under the Occupational Safety And Health Act, 29 U.S.C. 655, 657 to control bloodborne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste in the form of soiled garments and apparent would greatly facilitate compliance with the above-referenced Act.

Disposable medical utensils are generally composed of thermoplastics such as polyethylene, polypropylene, styrene, polyamides, acrylics, polyarimids, polyesters and cellulosics.

Although there is clearly a benefit in the use of disposables in medical care in that they reduce human contact with medical waste, non-biodegradable disposables are posing a disposability problem that is now being recognized. Landfill sites are becoming increasingly burdened with disposables which do not degrade for hundreds of years, if ever. As landfill sites become fully exploited, new sites must be found which are rightfully opposed by residents located proximate to proposed site locations. Medical waste incinerators are not available options to many generators.

It is thus an object of the present invention to provide disposable hot water soluble utensils that can be disposed of while avoiding additional burdens to landfill disposal sites and incinerators.

It is a further object of the present invention to provide a method of disposing of such utensils after use such that the utensils can be solubilized and medical waste substantially disinfected, in a single operation.

These and further objects will be more readily appreciated while considering the following disclosure and appended claims.

SUMMARY OF THE INVENTION

The present invention involves molded or formed articles that are disposable in hot water, and a method for disposing of such articles These articles are only water soluble at temperatures above the normal body temperature of approximately 37° C. and preferably above 50° C. and most preferably between approximately 80°–90° C. The utensils are subjected to water at a sufficient temperature to substantially dissolve them, whereupon the water and dissolved articles are subjected to disposal.

DETAILED DESCRIPTION OF THE INVENTION

The present invention deals with the disposal of molded, formed or extruded articles configured into a whole variety of suitable utensils such as specimen containers, bedpans, sponge bowls and containers, trays and emesis basins, blood bags, tubing and syringes. Such products are generally employed in the medical industry both in hospitals, outpatient facilities and home environments.

Many of these products generally come into contact with human bodily fluids and their disposal and disinfection has become a matter of major concern in light of the lack of biodegradability of prior products and the potential spread of human fluid-born diseases such as hepatitis B (HBV) and AIDS (HIV). As a consequence, utensils used herein may be molded from cellulosics such as Klucel™ from Aqualon Co. More preferably, polyvinyl alcohol can be employed and most preferably a polyvinyl alcohol polymer that has been highly crystallized to increase its temperature of water solubility. Crystallinity can also be enhanced by post annealing or "drawing" the polymer. Such utensils would be insoluble in cold to warm baths preferably below 37° C., the average temperature of the human body. However, it is preferred that at or near the boiling point of water, or at least above approximately 50° C. and preferably between 80°–90° C., disposal could be accomplished in a hot water bath such as a washing machine that is dedicated solely to solubilizing and disinfecting articles made of such water soluble polymers. By employing such a method, two objectives would be accomplished, namely, that the articles and utensils would be disinfected and would be solubilized for disposal through the sewer system. Not only would this lessen the burden now being imposed upon current landfill sites but liquid sewer disposal would prove a comparative low cost technique in ridding the user of such used utensils and would provide for point-of-generation disposal thus lessening opportunities for cross-infection.

Utensils useful in practicing the present method can be, for example:

Procedural trays, bowls and basins.

Laboratory ware including specimen containers, petridishes, pipettes, etc.

Patient care items including bedpans, urinals, medicine cups, glasses, feeding trays and kits.

Irrigation syringes and trays, catheritization trays, drainage bags.

Enema bags and buckets and tubing.

Utensils may be molded from propyl cellulose such as Klucel™ from Aqualon Company. More preferably, polyvinyl alcohol (PVA) can be employed and most preferred a copolymer of polyvinylacetate (PVAc) and polyvinyl alcohol can be used having the following formula:

$$[CH_2CH\ COOCH_2)_x(CH_2CH\ OH)_y]_z \quad (1)$$

Wherein Z (D.P.) is not less than 100,000 but preferably greater than 1,000,000, X is a minor fraction of the polymer, generally 0.00 wt % to 5.0 wt. % and Y is the balance. As such, the polymer can be entirely a homopolymer of polyvinyl alcohol. To increase its water solubility temperature, the polymer should be highly crystallized the degree of crystallization determining its solubility temperature.

The polymer of Eq. 1 is generally placticized with 0.05% to 5.0% polyethylene glycol or glycerine to control stability at melt temperature as the melt and disintegration temperatures are both near 200° C. without plasticizer present. The polymer of Eq. 1 may be blended with plasticizers, such as polyethylene glycols and polyglucosidics as required for processing purposes. But most practically, the polymer of Eq. 1 may be blended with the homopolymer polyvinylacetate (PVAc) in the range of 1–10 parts PVAc to 99 to 90 parts of the copolymer to produce a thermoplastic that can be plasticized with polyethylene glycol (PEG) and then molded, formed or extruded at 200°–220° C. without disintegration.

A commercial product Vinex™ 1003 (Air Products), which is a polyvinyl alcohol that has been highly crystallized by postdrawing and which has been plasticized with PEG and/or glycerine is useful for practicing this invention. It may be molded or formed or extruded at 215° C. without disintegration producing a utensil or article that solubilizes at 50° C. or greater in $H_2O$.

I claim:

1. A method of disposing of utensils after use said utensils comprising molded, formed or extruded articles being water soluble [tat] *at* temperatures only above 37° C., and not below 37° C., said method comprising subjecting said utensils after use to water at a sufficient temperature to substantially dissolve said utensils whereupon said water and dissolved utensils are subjected to disposal wherein said utensils are composed of one or more members selected from the group consisting of propyl cellulose, polyvinyl alcohol and copolymers of polyvinyl acetate and polyvinyl alcohol which have been highly crystallized by postdrawing or *by* heat annealing.

2. A method of disposing of utensils after use said utensils comprising molded, formed or extruded articles being water soluble at temperatures only above [37+ C] *37° C.*, and not below 37° C., said method comprising subjecting said utensils after use to water at a sufficient temperature to substantially dissolve said utensils whereupon said water and dissolved utensils are subjected to disposal wherein said utensils are composed of highly crystallized polyvinyl alcohol homopolymer, said crystallization being carried out by postdrawing or by heat annealing.

* * * * *